(12) United States Patent
Meng et al.

(10) Patent No.: US 10,481,140 B2
(45) Date of Patent: Nov. 19, 2019

(54) METHOD AND APPARATUS FOR CALIBRATING PARTICULATE MATTER MEASUREMENT VALUE

(71) Applicants: Beijing Xiaomi Mobile Software Co., Ltd., Haidian Street, Beijing (CN); Beijing Smartmi Technology Co., Ltd., Haidian Street, Beijing (CN)

(72) Inventors: Yanan Meng, Beijing (CN); Tiejun Liu, Beijing (CN); Dongxu Liu, Beijing (CN)

(73) Assignee: Beijing Xiaomi Mobile Software Co., Ltd., Beijing (CN)

( * ) Notice: Subject to any disclaimer, the term of this patent is extended or adjusted under 35 U.S.C. 154(b) by 131 days.

(21) Appl. No.: 15/684,632

(22) Filed: Aug. 23, 2017

(65) Prior Publication Data
US 2018/0059079 A1    Mar. 1, 2018

(30) Foreign Application Priority Data
Aug. 25, 2016  (CN) .......................... 2016 1 0729751

(51) Int. Cl.
*G01N 33/00*   (2006.01)
*G01N 15/06*   (2006.01)
(52) U.S. Cl.
CPC ......... *G01N 33/0006* (2013.01); *G01N 15/06* (2013.01)
(58) Field of Classification Search
None
See application file for complete search history.

(56) References Cited

U.S. PATENT DOCUMENTS 4,561,286 A * 12/1985 Sekler ................... G01B 7/066
                                                    177/210 FP
5,550,062 A *  8/1996 Wohltjen ............. G01N 29/022
                                                    436/155
(Continued)

FOREIGN PATENT DOCUMENTS

CN        101354332 A     1/2009
CN        104914022 A     9/2015
(Continued)

OTHER PUBLICATIONS

Extended European Search Report issued in corresponding European Patent Application No. 17187712.9 dated Jan. 5, 2018, 8 pages.
(Continued)

*Primary Examiner* — Natalie Huls
*Assistant Examiner* — Mohammed E Keramet-Amircolai
(74) *Attorney, Agent, or Firm* — Arch & Lake LLP

(57) ABSTRACT

A method and an apparatus are provided for calibrating a particulate matter measurement value. The method includes: when a current particulate matter measurement value is obtained, obtaining a current temperature-humidity parameter; obtaining a particulate matter measurement deviation value corresponding to the current temperature-humidity parameter from pre-stored particulate matter measurement deviation values under various temperature-humidity parameters according to the current temperature-humidity parameter; and calibrating the current particulate matter measurement value according to the particulate matter measurement deviation value corresponding to the current temperature-humidity parameter.

18 Claims, 9 Drawing Sheets

(56) References Cited

U.S. PATENT DOCUMENTS

| | | | | |
|---|---|---|---|---|
| 6,363,773 | B1* | 4/2002 | Bowers | G01N 29/022 |
| | | | | 310/313 D |
| 6,912,925 | B2* | 7/2005 | Cardelius | G01F 1/662 |
| | | | | 73/570 |
| 2014/0031263 | A1* | 1/2014 | Norling | G01N 5/02 |
| | | | | 506/35 |
| 2014/0130569 | A1* | 5/2014 | Doering | G01N 33/0006 |
| | | | | 73/1.06 |
| 2014/0238101 | A1* | 8/2014 | Mealy, Jr. | G01N 33/007 |
| | | | | 73/1.06 |
| 2015/0276695 | A1* | 10/2015 | Kaneblei | G01N 33/0006 |
| | | | | 73/1.06 |
| 2015/0323511 | A1* | 11/2015 | Hendry | A61B 5/1495 |
| | | | | 73/1.06 |
| 2016/0010453 | A1* | 1/2016 | Breviere | G01N 30/88 |
| | | | | 175/40 |
| 2016/0041137 | A1* | 2/2016 | Brahma | G01M 15/102 |
| | | | | 73/1.06 |
| 2016/0131625 | A1* | 5/2016 | Furton | A01K 15/02 |
| | | | | 73/1.06 |
| 2017/0336313 | A1 | 11/2017 | Iglseder | |

FOREIGN PATENT DOCUMENTS

| | | |
|---|---|---|
| DE | 102014017220 A1 | 5/2016 |
| GB | 2390161 A | 12/2003 |
| WO | 2010074812 A1 | 7/2010 |

OTHER PUBLICATIONS

Chinese Office Action (including English translation) issued in CN Application No. 201610729751.6, dated Aug. 28, 2018, 22 pages.

* cited by examiner

METHOD AND APPARATUS FOR CALIBRATING PARTICULATE MATTER MEASUREMENT VALUE

CROSS-REFERENCE TO RELATED APPLICATION

This application claims priority to and benefits of Chinese Patent Application Serial No. CN201610729751.6, filed with the State Intellectual Property Office of P. R. China on Aug. 25, 2016, the entire content of which is incorporated herein by reference.

FIELD

The present disclosure relates to the field of terminal technology, and more particularly, to a method and an apparatus for calibrating a particulate matter measurement value.

BACKGROUND

Air pollution is a substantial problem for many developing countries. One type of air pollution is caused by particulate matter that contains microscopic solids or liquid droplets, which can be inhaled and cause serious health problems.

Particulate matter (PM) may also be called particle pollution, which is a mixture of solid particles and liquid droplets found in the air. Some particles, such as dust, dirt, soot, or smoke, are large or dark enough to be seen with the naked eye. Others are so small they can only be detected using an electron microscope or other instruments. Currently, to measure the level of particulate matter (such as PM2.5, PM10, and other fine particles) in the air, a variety of particulate matter measuring instruments have been introduced, for example, portable haze detectors. However, particulate matter measurement values obtained by these particulate matter measuring instruments may generally be affected by the temperature and the humidity. Thus, the particulate matter measurement value may not be accurate. There is a need for better measurement methods and devices to obtain more accurate PM measurement values.

SUMMARY

A method and an apparatus for calibrating a particulate matter measurement value are provided in the present disclosure. The technical solutions are as follows.

According to a first aspect of the present disclosure, a method for calibrating a particulate matter measurement value is provided. The method may include: obtaining a current particulate matter measurement value and obtaining a current temperature-humidity parameter associated with the current particulate matter measurement value; obtaining a particulate matter measurement deviation value corresponding to the current temperature-humidity parameter from pre-stored particulate matter measurement deviation values corresponding to various temperature-humidity parameters according to the current temperature-humidity parameter; calibrating the current particulate matter measurement value according to the particulate matter measurement deviation value corresponding to the current temperature-humidity parameter.

According to a second aspect of the present disclosure, an apparatus for calibrating a particulate matter measurement value is provided. The apparatus may include: a first obtaining module, configured to obtain a current temperature-humidity parameter when a current particulate matter measurement value is obtained; a second obtaining module, configured to obtain a particulate matter measurement deviation value corresponding to the current temperature-humidity parameter from pre-stored particulate matter measurement deviation values corresponding to various temperature-humidity parameters according to the current temperature-humidity parameter; a calibrating module, configured to calibrate the current particulate matter measurement value according to the particulate matter measurement deviation value corresponding to the current temperature-humidity parameter.

According to a third aspect of the present disclosure, a device is provided for calibrating a particulate matter measurement value. The device may include a processor and a memory configured to store instructions executable by the processor, in which, the processor is configured to perform the method for calibrating a particulate matter measurement value according to embodiments of the first aspect of the present disclosure.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments consistent with the disclosure and, together with the description, serve to explain the principles of the disclosure.

DETAILED DESCRIPTION

Reference will now be made in detail to exemplary embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the disclosure. Instead, they are merely examples of apparatuses and methods consistent with aspects related to the disclosure as recited in the appended claims.

Currently, to measure the level of particulate matter (such as PM2.5, PM10, and other fine particles) in the air, a lot of particulate matter measuring instruments have been introduced, for example, portable haze detectors. However, particulate matter measurement values obtained by these particulate matter measuring instruments may generally be affected by the temperature and the humidity, and therefore the particulate matter measurement values may be not accurate.

Figure 1:
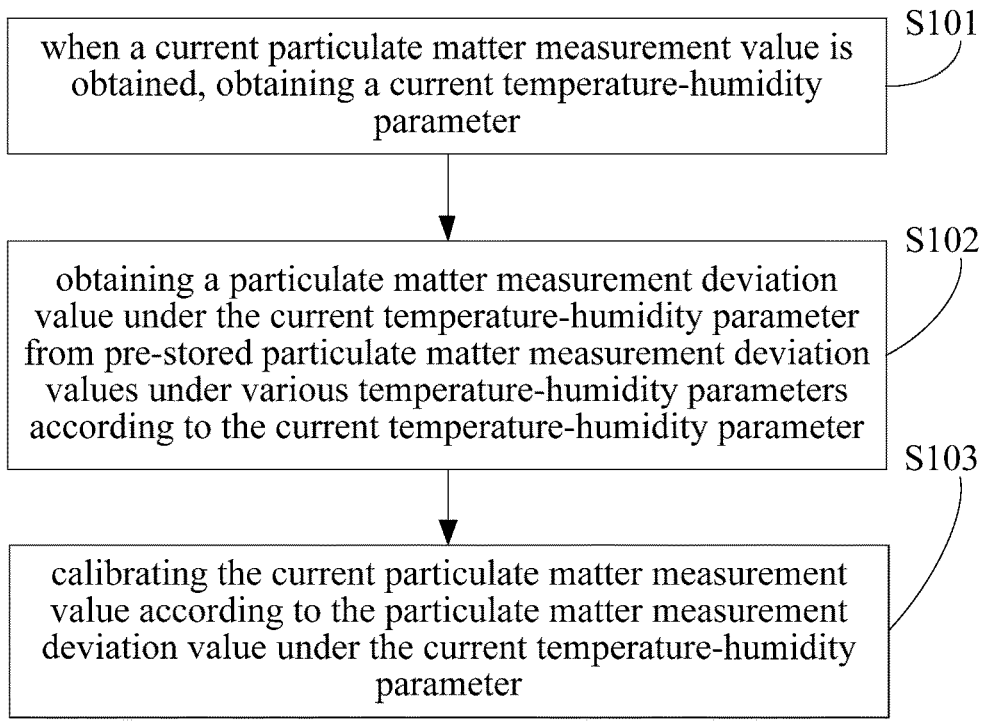
FIG. 1 is a flow chart showing a method for calibrating a particulate matter measurement value according to one or more aspects of the present disclosure.

To address the above technical problems, a method for calibrating a particulate matter measurement value is provided in the present disclosure. The method may be used in a calibration procedure, system, or apparatus for a particulate matter measurement value. The method may be implemented by an apparatus or device. The device may be a terminal for measuring level of particulate matter (i.e. a terminal having a particulate matter measuring sensor) or a device configured to be connected to a terminal capable of measuring the level of the particulate matter. As shown in FIG. 1, the method may include at least following actions S101 to S103.

At block S101, a current temperature-humidity parameter is obtained when a current particulate matter measurement value is obtained, in which the particulate matter may include PM2.5 (fine particulate matter), PM10 (inhalable particulate matter) or other fine particles. The current temperature-humidity parameter may be obtained using a first sensor while the current particulate matter measurement value may be obtained using a second sensor. Both sensors may be integrated in one integrated circuit or separate hardware modules. In some embodiments, the device may only have one sensor installed on the device when the temperature-humidity parameter is available online. For example, the current temperature-humidity parameter may be associated with the current particulate matter measurement value because both of them are tied to environmental conditions at the same location during the same time period.

The current particulate matter measurement value refers to a particulate matter level in the air measured under the current temperature-humidity parameter. The current temperature-humidity parameter may be a combination of a current temperature parameter and a current humidity parameter, and include the current temperature parameter and the current humidity parameter, in which the current humidity parameter may be a relative humidity or an absolute humidity.

At block S102, a particulate matter measurement deviation value under the current temperature-humidity parameter is obtained from pre-stored particulate matter measurement deviation values under various temperature-humidity parameters. The term "under" may be understood as "corresponding to" in the disclosure. Here, the particulate matter measurement deviation value corresponding to the current temperature-humidity parameter is obtained from pre-stored particulate matter measurement deviation values corresponding to various temperature-humidity parameters using the current temperature-humidity parameter.

The particulate matter measurement deviation value corresponding to a temperature-humidity parameter is configured to characterize a difference between an actual particulate matter measurement value and a true value of the particulate matter level under the temperature-humidity parameter.

In addition, to find particulate matter measurement deviation values under different temperature-humidity parameters, particulate matter measurement deviation values under various temperature-humidity parameters may be obtained and stored in advance as much as possible.

Furthermore, when the current temperature-humidity parameter is different from each of the stored temperature-humidity parameters, a particulate matter measurement deviation value corresponding to a temperature-humidity parameter that is most close to the current temperature-humidity parameter may be obtained and considered as the particulate matter measurement deviation value under the current temperature-humidity parameter, thus obtaining the nearest particulate matter measurement deviation value under the current temperature-humidity parameter.

At block S103, the current particulate matter measurement value is calibrated according to the particulate matter measurement deviation value corresponding to the current temperature-humidity parameter.

When the current temperature-humidity parameter is obtained, the current particulate matter measurement deviation value may be automatically obtained from the pre-stored particulate matter measurement deviation values under various temperature-humidity parameters, so that the current particulate matter measurement value may be calibrated precisely according to the particulate matter measurement deviation value under the current temperature-humidity parameter. Therefore, a normal particulate matter measurement value under the current temperature-humidity parameter may be obtained, and the user can know exactly the normal particulate matter measurement value under the current temperature-humidity parameter.

Figure 2:
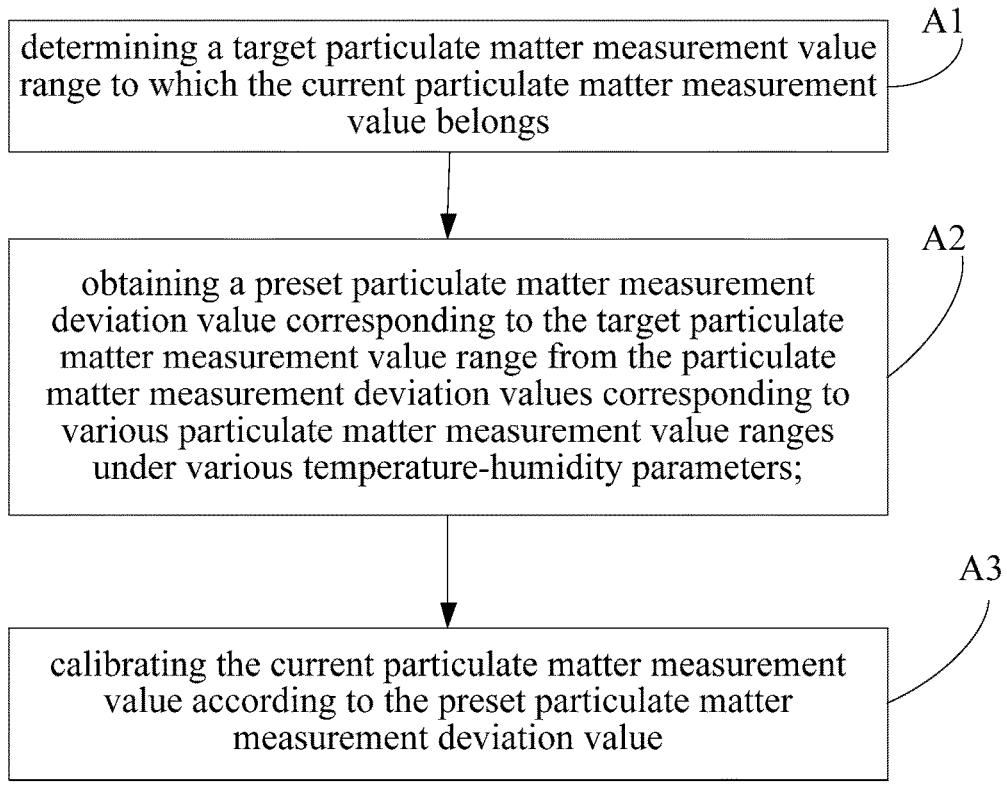
FIG. 2 is a flow chart showing a method for calibrating a particulate matter measurement value according to one or more aspects of the present disclosure.

As shown in FIG. 2, in one or more embodiments, the particulate matter measurement deviation values under different temperature-humidity parameters may further include particulate matter measurement deviation values corresponding to different particulate matter measurement value ranges under different temperature-humidity parameters. Here, the particulate matter measurement value ranges may be set by the user according to requirements. For example, the user may select from ranges, which may be divided by the user according to air quality levels.

Since there may be different particulate matter measurement value ranges under different temperature-humidity parameters, the particulate matter measurement deviation values under different temperature-humidity parameters may include the particulate matter measurement deviation values corresponding to different particulate matter measurement value ranges under different temperature-humidity parameters, such that the particulate matter measurement deviation values in different particulate matter measurement value ranges may be found quickly.

The block S103 in FIG. 1 may be performed as follows.

At block A1, a target particulate matter measurement value range to which the current particulate matter measurement value belongs is determined.

The current particulate matter measurement value is a particulate matter measurement value measured under the current temperature-humidity parameter, and therefore the target particulate matter measurement value range to which the current particulate matter measurement value belongs is the particulate matter measurement value range where the current particulate matter measurement value is located in under the current temperature-humidity parameter.

In detail, the target particulate matter measurement value range may be a particulate matter measurement value range containing the current particulate matter measurement value and having a correspondence relationship with the current particulate matter measurement value.

At block A2, a preset particulate matter measurement deviation value corresponding to the target particulate matter measurement value range is obtained from the particulate matter measurement deviation values corresponding to different particulate matter measurement value ranges under different temperature-humidity parameters.

In one or more embodiments, the temperature-humidity parameters, the particulate matter measurement value ranges and the particulate matter measurement deviation values corresponding to thereto may be stored in a form of table. As a non-limiting example, the temperature-humidity parameters may have a data structure with a storage format as: [temperature parameter; humidity parameter; particulate matter measurement value range; particulate matter measurement deviation value].

At block A3, the current particulate matter measurement value is calibrated according to the preset particulate matter measurement deviation value.

When the target particulate matter measurement value range is obtained, the preset particulate matter measurement deviation value corresponding to the target particulate matter measurement value range may be automatically obtained from the particulate matter measurement deviation values corresponding to different particulate matter measurement value ranges under various temperature-humidity parameters. Accordingly, the current particulate matter measurement value may be calibrated precisely according to the preset particulate matter measurement deviation value. Therefore, a normal particulate matter measurement value under the current temperature-humidity parameter may be obtained, which may give the user can a better idea about the normal particulate matter measurement value under the current temperature-humidity parameter.

Figure 3:
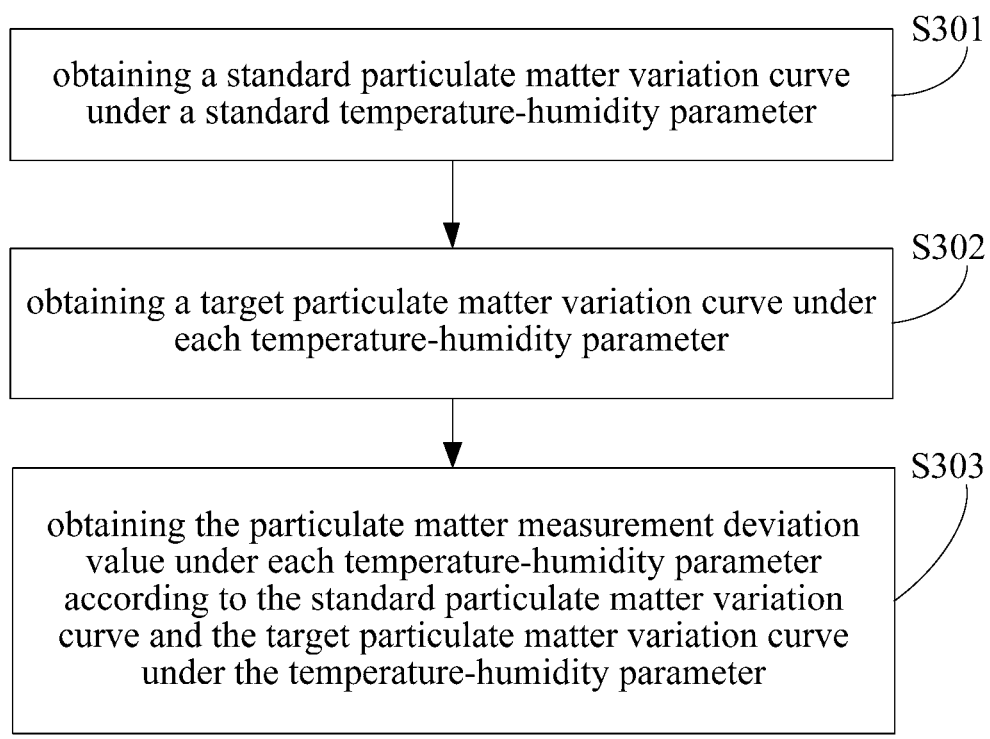
FIG. 3 is a flow chart showing a method for calibrating a particulate matter measurement value according to one or more aspects of the present disclosure.

As shown in FIG. 3, in one or more embodiments, before block S102 in FIG. 1, the method may further include following actions.

At block S301, a standard particulate matter variation curve under a standard temperature-humidity parameter is obtained, in which the standard particulate matter variation curve represents a relationship between the particulate matter measurement values and time under the standard temperature-humidity parameter.

For example, the standard temperature-humidity parameter may be set by the manufacturer according to a performance of a terminal device for measuring the particulate matter level such as a haze detector. The standard temperature-humidity parameter may be a combination of a temperature parameter and a humidity parameter, under which the terminal device has a relatively more accurate measurements (i.e. an ideal combination of temperature and humidity parameters for the terminal device).

In addition, the standard particulate matter variation curve may be obtained as follows.

In an environment with a preset standard temperature and a present standard humidity, the device for measuring the particulate matter measurement value is put into an experiment box. Then, a certain amount of PM2.5 standard dust is blown into the experiment box. With natural sedimentation of the PM2.5 standard dust, the change of PM 2.5 values with respect to time may be recorded as the standard particulate matter variation curve. For the standard particulate matter variation curve, X-axis represents time, Y-axis represents the PM 2.5 value (i.e. the particulate matter measurement value). Of course, there may be a Z-axis which represents the preset standard temperature and standard humidity.

Here, when obtaining the standard particulate matter variation curve, manual intervention may be needed on the experimental box. The experimental box itself has a gap. When the PM2.5 standard dust is blown into the experimental box, the gap is closed. After the PM2.5 standard dust is completely blown into the box, the gap is not closed (i.e. opened), so that the PM2.5 standard dust may disperse in the process of sedimentation, thus simulating the natural landing and dispersing process of the PM2.5 in the air.

At block S302, a target particulate matter variation curve under each temperature-humidity parameter is obtained, in which the target particulate matter variation curve represents a relationship between the particulate matter measurement values and the time under the temperature-humidity parameter. The various temperature-humidity parameters may include combinations of common temperature parameters and common humidity parameters according to statistic results.

The process of obtaining the target particulate matter variation curve is similar to the process of obtaining the standard particulate matter variation curve. Details are as follows.

In an environment with a preset temperature and humidity, the device for measuring the particulate matter measurement value is put into an experiment box. Then, a same amount of PM2.5 standard dust with that for obtaining the standard particulate matter variation curve is blown into the experiment box. With natural sedimentation of the PM2.5 standard dust, the change of PM 2.5 values with respect to time may be recorded as the target particulate matter variation curve. For the target particulate matter variation curve, X-axis represents time, Y-axis represents the PM 2.5 value (i.e. the particulate matter measurement value). Of course, there may be a Z-axis which represents the preset temperature and humidity. Similarly, under different temperature and humidity, different target particulate matter variation curves may be obtained.

Here, when obtaining the target particulate matter variation curve, manual intervention may be needed on the experimental box. The experimental box itself has a gap. When the PM2.5 standard dust is blown into the experimental box, the gap is closed. After the PM2.5 standard dust is completely blown into the box, the gap is not closed (i.e. opened), so that the PM2.5 standard dust may disperse in the process of sedimentation, thus simulating the natural landing and dispersing process of the PM2.5 in the air.

At block S303, the particulate matter measurement deviation value under a temperature-humidity parameter is obtained according to the standard particulate matter variation curve and the target particulate matter variation curve under the temperature-humidity parameter.

In some embodiments, the particulate matter measurement deviation value under each temperature-humidity parameter is obtained according to the standard particulate matter variation curve and the target particulate matter variation curve under each temperature-humidity parameter. When the standard particulate matter variation curve and the target particulate matter variation curve are obtained, a difference between the standard particulate matter variation curve and the target particulate matter variation curve may be calculated so as to obtain the particulate matter measurement deviation value.

In one or more embodiments, the block S303 in FIG. 3 may be performed as follows.

A percentage difference variation curve of particulate matter measurement values under a temperature-humidity parameter may be obtained according to the standard particulate matter variation curve and target particulate matter variation curve, in which the percentage difference variation curve represents a relationship of a percentage difference between the standard particulate matter variation curve and the target particulate matter variation curve to time.

When obtaining the percentage difference variation curve, for each time point, a difference value between the particulate matter measurement value under the standard temperature-humidity parameter and the particulate matter measurement value under each temperature-humidity parameter may be obtained first, and then a quotient of the difference value to the particulate matter measurement value under the standard temperature-humidity parameter at the same time point is calculated.

In detail, at each time point, the percentage difference corresponding to the particulate matter measurement value under each temperature-humidity parameter=(the particulate matter measurement value under the temperature-humidity parameter−the particulate matter measurement value under the standard temperature-humidity parameter)/the particulate matter measurement value under the standard temperature-humidity parameter.

The quotient is the percentage difference corresponding to the particulate matter measurement value under the temperature-humidity parameter, and the percentage difference variation curves of particulate matter measurement values under various temperature-humidity parameters may be depicted according to the percentage differences corresponding to various temperature-humidity parameters.

The particulate matter measurement deviation value under at least one temperature-humidity parameter is determined according to the percentage difference variation curve under the at least one temperature-humidity parameter.

In some embodiments, the particulate matter measurement deviation value under each temperature-humidity parameter is determined according to the percentage difference variation curve under each temperature-humidity parameter. That is, once the percentage difference variation curve under each temperature-humidity parameter is obtained, the particulate matter measurement deviation value under each temperature-humidity parameter may be determined accordingly.

In one or more embodiments, the particulate matter measurement deviation value under each temperature-humidity parameter determined according to the percentage difference variation curve under each temperature-humidity parameter is a percentage difference of the particulate matter measurement value under each temperature-humidity parameter.

Figure 4:
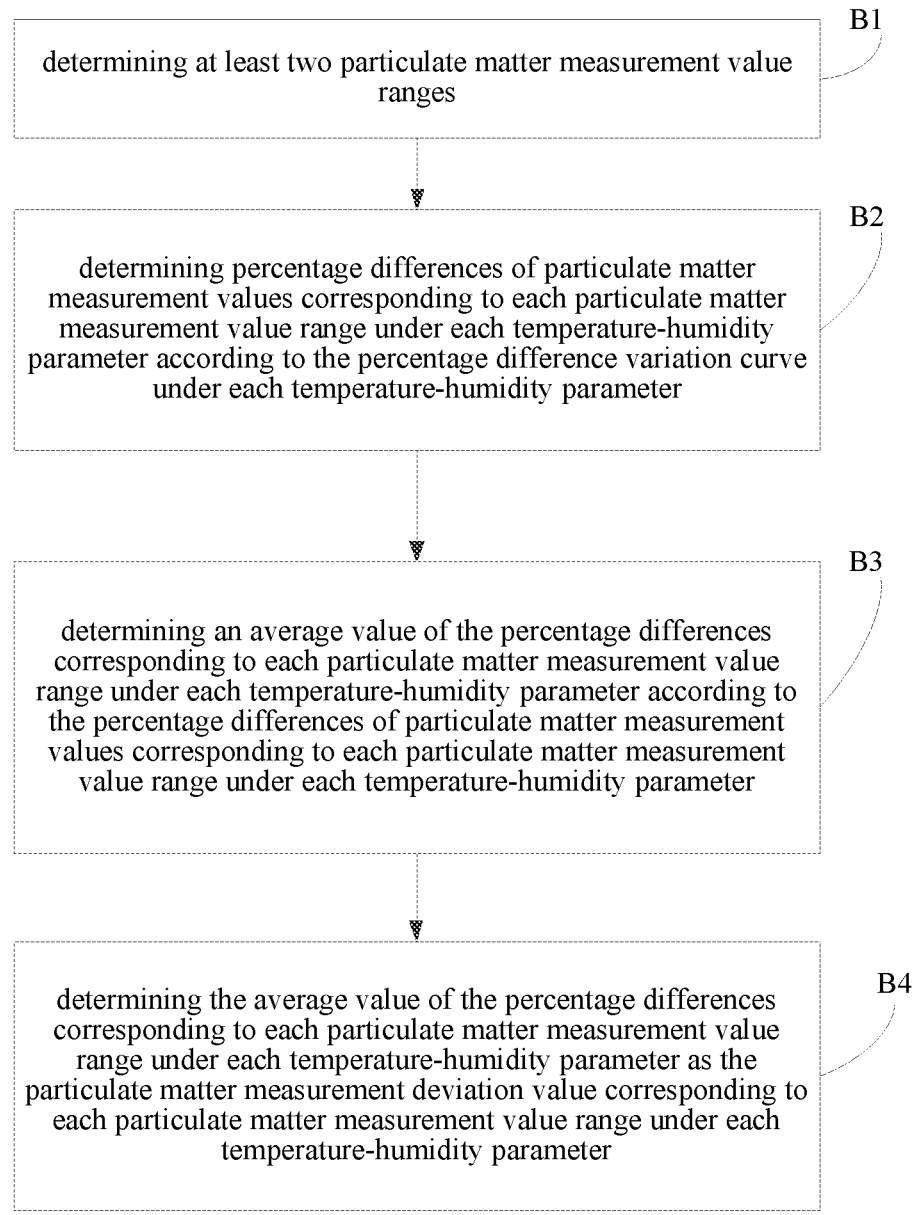
FIG. 4 is a flow chart showing a method for calibrating a particulate matter measurement value according to one or more aspects of the present disclosure.

As shown in FIG. 4, in one or more embodiments, the above action of "determining particulate matter measurement deviation value under each temperature-humidity parameter according to the percentage difference variation curve under each temperature-humidity parameter" may be performed as follows.

At block B1, at least two particulate matter measurement value ranges are determined.

When determining the at least two particulate matter measurement value ranges, the particulate matter measurement value ranges may be divided according to an air quality level, as shown in Table 1.

TABLE 1

| Air quality levels | PM2.5 average value (particulate matter measurement value range) in 24 hours |
| --- | --- |
| excellent | 0~35 μg/m³ |
| good | 35~75 μg/m³ |
| Mild contamination | 75~115 μg/m³ |
| Moderately polluted | 115~150 μg/m³ |
| Severe pollution | 150~250 μg/m³ |
| Serious pollution | Greater than or equal to 250 μg/m³ |

In addition, since the at least two particulate matter measurement value ranges are determined according to air quality levels, the determined at least two particulate matter measurement value ranges may apply to not only the standard temperature-humidity parameter but also various different temperature-humidity parameters. That is, the particulate matter measurement value ranges corresponding to the percentage variation difference curve under a temperature-humidity parameter may be the same as the particulate matter measurement value ranges corresponding to the percentage difference variation curve under the standard temperature-humidity parameter.

At block B2, percentage differences of particulate matter measurement values corresponding to each particulate matter measurement value range under each temperature-humidity parameter are determined according to the percentage difference variation curve under each temperature-humidity parameter.

For the target particulate matter variation curve under each temperature-humidity parameter, the lateral axis represents the time, and the vertical axis represents the particulate matter measurement value corresponding to each time point under the temperature-humidity parameter. Thus, when determining the percentage differences of particulate matter measurement values corresponding to each particulate matter measurement value range under each temperature-humidity parameter, the particulate matter measurement values in each particulate matter measurement value range under each temperature-humidity parameter may be determined first according to the target particulate matter variation curve under each temperature-humidity parameter. Then a time range to which each particulate matter measurement value may be determined, and the percentage differences of particulate matter measurement values under each time range may be determined according to the percentage difference variation curve under each temperature-humidity parameter.

That is, percentage differences of particulate matter measurement values corresponding to each particulate matter measurement value range under each temperature-humidity parameter are determined. For example, assuming the temperature-humidity parameter is combination A (e.g. temperature a and humidity b), then when determining percentage differences of particulate matter measurement values corresponding to the particulate matter measurement value range B under combination A, the particulate matter measurement values in the particulate matter measurement value range B under combination A may be determined first according to the target particulate matter variation curve C under combination A. Then, a time range D to which the time points corresponding to the particulate matter measurement values in the particulate matter measurement value range B belong may be determined according to the target particulate matter variation curve C. Finally, the percentage differences of particulate matter measurement values corresponding to respective time points in the time range D may be obtained according to the percentage difference variation curve under combination A. That is, percentage differences of particulate matter measurement values corresponding to the particulate matter measurement value range B under combination A are obtained.

At block B3, an average value of the percentage differences corresponding to each particulate matter measurement value range under each temperature-humidity parameter is determined according to the percentage differences of particulate matter measurement values corresponding to each particulate matter measurement value range under each temperature-humidity parameter.

At block B4, the average value of the percentage differences corresponding to each particulate matter measurement value range under each temperature-humidity parameter is determined as the particulate matter measurement deviation value corresponding to each particulate matter measurement value range under each temperature-humidity parameter.

In the percentage difference variation curve under each temperature-humidity parameter, the vertical axis represents the percentage differences of particulate matter measurement values at different time points. Because the particulate matter may sediment or disperse as time goes, there may be more than one percentage differences under various temperature-humidity parameters. Therefore, at least two particulate matter measurement value ranges may be determined, so that an average value of the percentage differences corresponding to each particulate matter measurement value range under each temperature-humidity parameter is determined. Additionally or alternatively, the average value of the percentage differences corresponding to each particulate matter measurement value range under each temperature-humidity parameter may further be determined as the particulate matter measurement deviation value corresponding to each particulate matter measurement value range under each temperature-humidity parameter, thereby making the particulate matter measurement deviation values corresponding to various temperature-humidity parameters more concrete and precise, i.e., making each particulate matter measurement value range under each temperature-humidity parameter have a corresponding particulate matter measurement deviation value, and further making it convenient to find the particulate matter measurement deviation values under various temperature-humidity parameters later.

In one or more embodiments, the method further includes storing three sets of data: the various temperature-humidity parameters, the various particulate matter measurement value ranges, and the average values of percentage differences corresponding to various particulate matter measurement value ranges in a correspondence relationship.

By storing the three sets of data in the correspondence relationship, it may be convenient to obtain the average value of percentage differences corresponding to the current particulate matter measurement value range and the current temperature-humidity parameter according to the current temperature-humidity parameter and the particulate matter measurement value range to which the current particulate matter measurement value belongs, in the subsequent using. In other words, the particulate matter measurement deviation value under the current temperature-humidity parameter is the average value of percentage differences corresponding to the target particulate matter measurement value range to which the current particulate matter measurement value belongs under the current temperature-humidity parameter.

Figure 5:
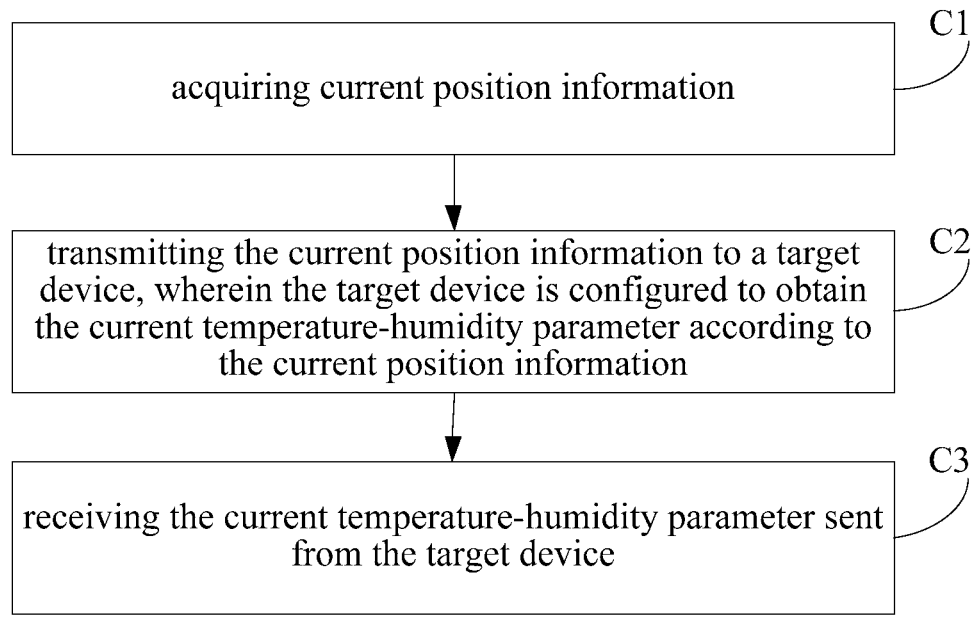
FIG. 5 is a flow chart showing a method for calibrating a particulate matter measurement value according to one or more aspects of the present disclosure.

As shown in FIG. 5, in one or more embodiments, the block S101 in FIG. 1 may be performed as follows.

At block C1, current position information is obtained.

At block C2, the current position information is transmitted to a target device, in which the target device is configured to obtain the current temperature-humidity parameter according to the current position information. The target device may be a device bound to the device that can inquire the current temperature parameter and the current humidity parameter according to the current position information. For example, the target device may be a server or a temperature sensor in direct communication with the device.

At block C3, the current temperature-humidity parameter sent from the target device is received.

Here, the device may obtain the current position information, and transmit the current position information to the target device to obtain the current temperature-humidity parameter by the target device. Thus, there is no need to install any temperature sensor or humidity sensor in the device, thus reducing the size of the device.

In addition, when the device is a device which can detect the current particulate matter measurement value by itself through a built-in particulate matter sensor (such as a PM2.5 sensor), obtaining the current temperature-humidity parameter by the target device may also prevent the mutual interference between the particulate matter sensor and the temperature or humidity sensors that need to be installed in the device, which causes inaccurate measurement values of these sensors. For example, when a built-in temperature-humidity sensor is introduced, the particulate matter measurement value may be affected by heat generated by the sensor, which may be avoided by obtaining the current temperature-humidity parameter by the target device without installing the temperature-humidity sensor in the device.

In one or more embodiments, before block S102 in FIG. 1 is executed, the method may further include following actions.

A plurality of preset temperature parameters and a plurality of preset humidity parameters are obtained.

The plurality of preset temperature parameters and the plurality of preset humidity parameters are grouped so as to obtain various temperature-humidity parameters.

For obtaining the various temperature-humidity parameters, a plurality of preset temperature parameters and a plurality of preset humidity parameters which are common in local (i.e., where the terminal such as the haze detector for measuring particulate matter level is located) may be obtained, and the plurality of preset temperature parameters and the plurality of preset humidity parameters are automatically grouped, so as to obtain the various temperature-humidity parameters.

Additionally or alternatively, when obtaining various temperature-humidity parameters, a plurality of common combinations of the local temperature parameters and humidity parameters may also be determined as the various temperature-humidity parameters.

Here, since the most common combinations of the local temperature parameters and humidity parameters may be different in four seasons of a year, the various temperature-humidity parameters may change according to the seasons. Similarly, for different areas, the most common combinations of the local temperature parameters and the humidity parameters may be different, and thus the temperature-humidity parameters may change with different areas.

Figure 6:
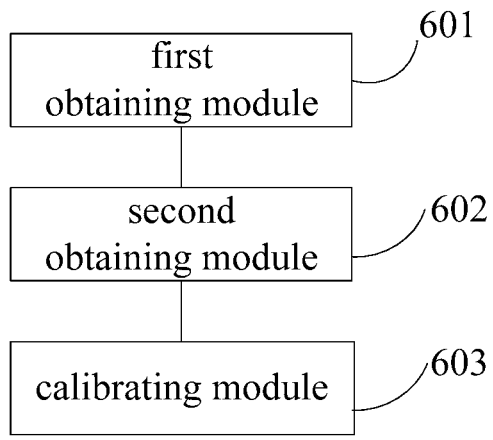
FIG. 6 is a block diagram illustrating an apparatus for calibrating a particulate matter measurement value according to one or more aspects of the present disclosure.

Corresponding to the method for calibrating a particulate matter measurement value provided in above embodiments of the present disclosure, an apparatus for calibrating a particulate matter measurement value is further provided. As shown in FIG. 6, the apparatus includes a first obtaining module 601, a second obtaining module 602 and a calibrating module 603.

The first obtaining module 601 is configured to obtain a current temperature-humidity parameter when a current particulate matter measurement value is obtained.

The second obtaining module 602 is configured to obtain a particulate matter measurement deviation value under the current temperature-humidity parameter from pre-stored particulate matter measurement deviation values under various temperature-humidity parameters.

The calibrating module 603 is configured to calibrate the current particulate matter measurement value according to the particulate matter measurement deviation value under the current temperature-humidity parameter.

Figure 7:
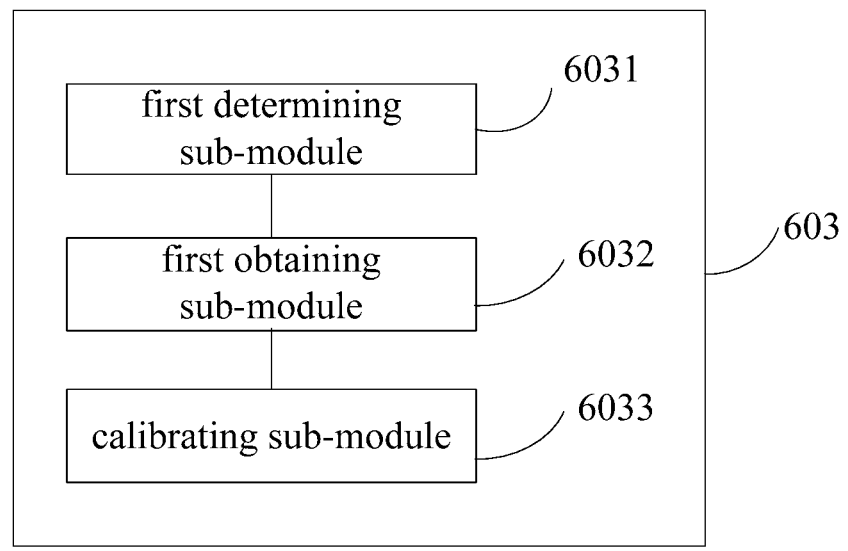
FIG. 7 is a block diagram illustrating an apparatus for calibrating a particulate matter measurement value according to one or more aspects of the present disclosure.

As shown in FIG. 7, in one or more embodiments, the particulate matter measurement deviation values under different temperature-humidity parameters may further include particulate matter measurement deviation values corresponding to various particulate matter measurement deviation value ranges under various temperature-humidity parameters.

The calibrating module 603 may include a first determining sub-module 6031, a first obtaining sub-module 6032 and a calibrating sub-module 6033.

The first determining sub-module 6031 is configured to determine a target particulate matter measurement value range to which the current particulate matter measurement value belongs.

The first obtaining sub-module 6032 is configured to obtain a preset particulate matter measurement deviation value corresponding to the target particulate matter measurement value range from the particulate matter measurement deviation values corresponding to different particulate matter measurement ranges under different temperature-humidity parameters.

The calibrating sub-module 6033 is configured to calibrate the current particulate matter measurement value according to the preset particulate matter measurement deviation value.

Figure 8:
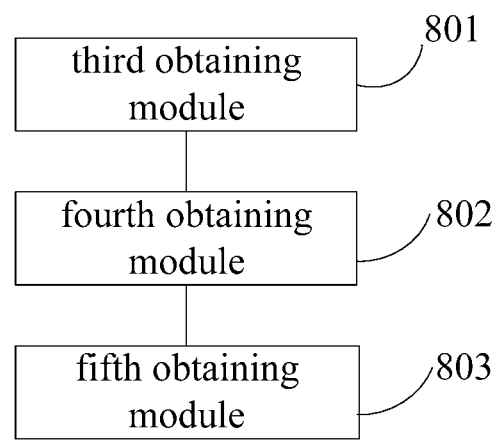
FIG. 8 is a block diagram illustrating an apparatus for calibrating a particulate matter measurement value according to one or more aspects of the present disclosure.

As shown in FIG. 8, in one or more embodiments, the apparatus may further include a third obtaining module 801, a fourth obtaining module 802 and a fifth obtaining module 803.

The third obtaining module 801 is configured to obtain a standard particulate matter variation curve under a standard temperature-humidity parameter, in which the standard particulate matter variation curve represents a relationship between the particulate matter measurement values and the time under the standard temperature-humidity parameter.

The fourth obtaining module 802 is configured to obtain a target particulate matter variation curve under each temperature-humidity parameter, in which the target particulate matter variation curve represents a relationship between the particulate matter measurement values and the time under the temperature-humidity parameter.

The fifth obtaining module 803 is configured to obtain the particulate matter measurement deviation value under each temperature-humidity parameter according to the standard particulate matter variation curve and the target particulate matter variation curve under each temperature-humidity parameter.

Figure 9:
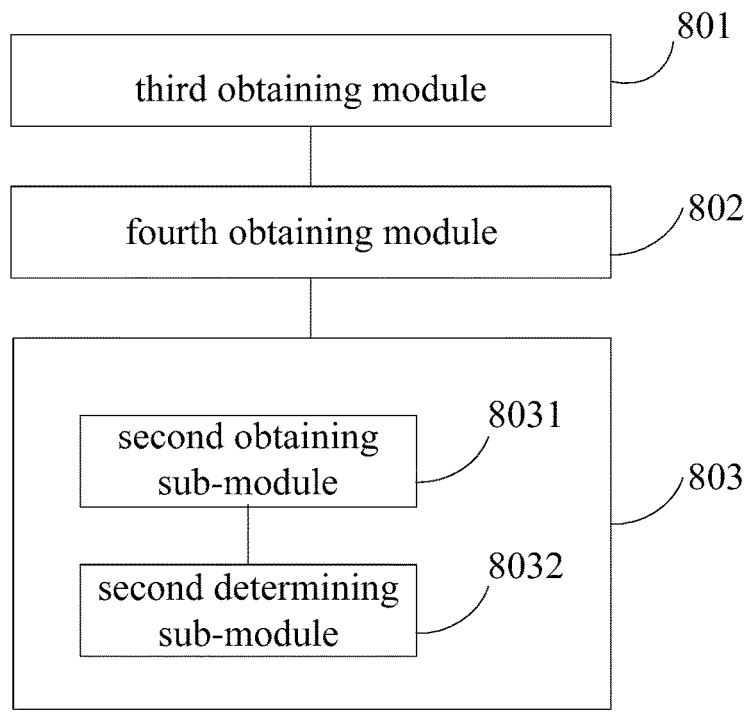
FIG. 9 is a block diagram illustrating an apparatus for calibrating a particulate matter measurement value according to one or more aspects of the present disclosure.

As shown in FIG. 9, in one or more embodiments, the fifth obtaining module 803 illustrated in FIG. 8 may include a second obtaining sub-module 8031 and a second determining sub-module 8032.

The second obtaining sub-module 8031 is configured to obtain a percentage difference variation curve of a particulate matter measurement value under each temperature-humidity parameter according to the standard particulate matter variation curve and target particulate matter variation curve, wherein the percentage difference variation curve represents a relationship of a percentage difference between the standard particulate matter variation curve and the target particulate matter variation curve to time.

The second determining sub-module 8032 is configured to determine the particulate matter measurement deviation value under each temperature-humidity parameter according to the percentage difference variation curve under each temperature-humidity parameter.

Figure 10:
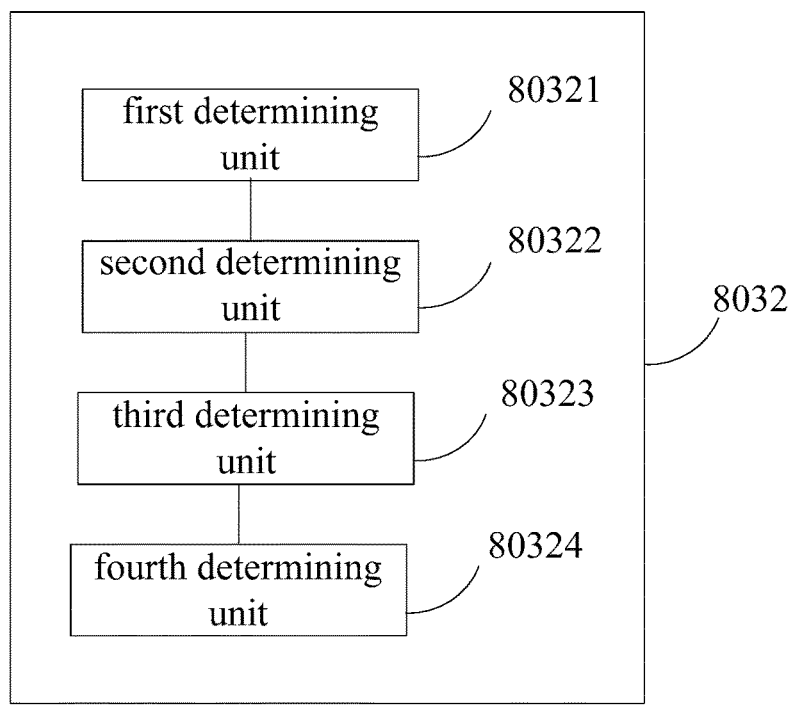
FIG. 10 is a block diagram illustrating an apparatus for calibrating a particulate matter measurement value according to one or more aspects of the present disclosure.

As shown in FIG. 10, in one or more embodiments, the second determining sub-module 8032 illustrated in FIG. 9 may include a first determining unit 80321, a second determining unit 80322, a third determining unit 80323, and a fourth determining unit 80324.

The first determining unit 80321 is configured to determine at least two particulate matter measurement value ranges.

The second determining unit 80322 is configured to determine percentage differences of particulate matter measurement values corresponding to each particulate matter measurement value range under each temperature-humidity parameter according to the percentage difference variation curve under each temperature-humidity parameter.

The third determining unit 80323 is configured to determine an average value of the percentage differences corresponding to each particulate matter measurement value range under each temperature-humidity parameter according to the percentage differences of particulate matter measurement values corresponding to each particulate matter measurement value range under each temperature-humidity parameter.

The fourth determining unit 80324 is configured to determine the average value of the percentage differences corresponding to each particulate matter measurement value range under each temperature-humidity parameter as the particulate matter measurement deviation value corresponding to each particulate matter measurement value range under each temperature-humidity parameter.

Figure 11:
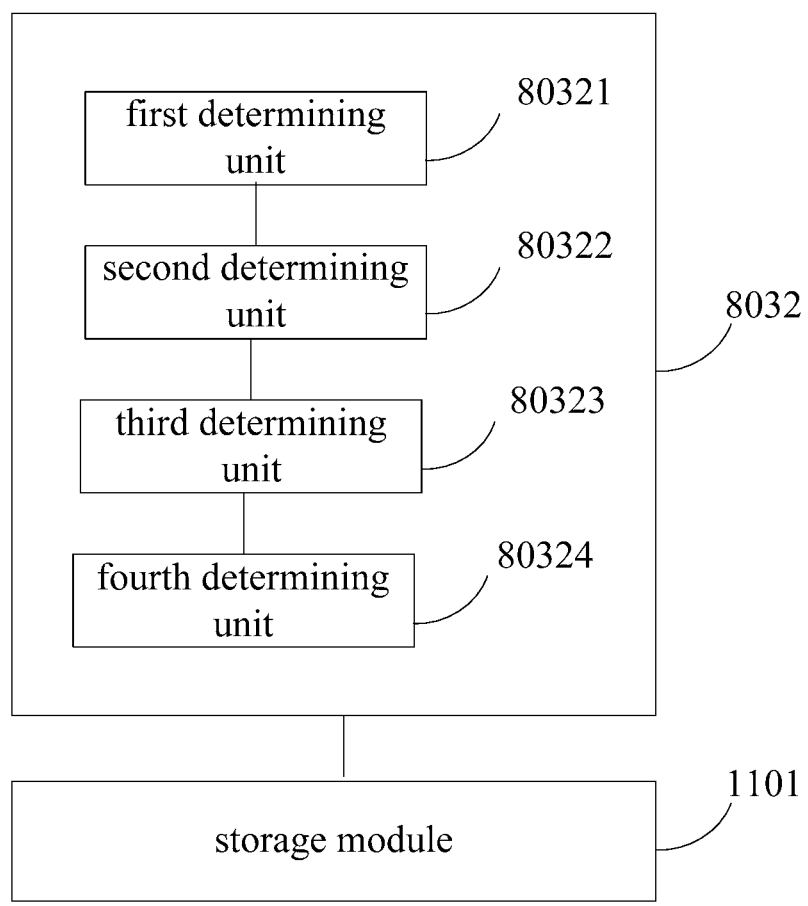
FIG. 11 is a block diagram illustrating an apparatus for calibrating a particulate matter measurement value according to one or more aspects of the present disclosure.

As shown in FIG. 11, in one or more embodiments, the apparatus illustrated in FIG. 10 may further include a storage module 1101. The storage module 1101 is configured to store the various temperature-humidity parameters, the various particulate matter measurement value ranges and the average values of percentage differences corresponding to various particulate matter measurement value ranges in a correspondence relationship.

Figure 12:
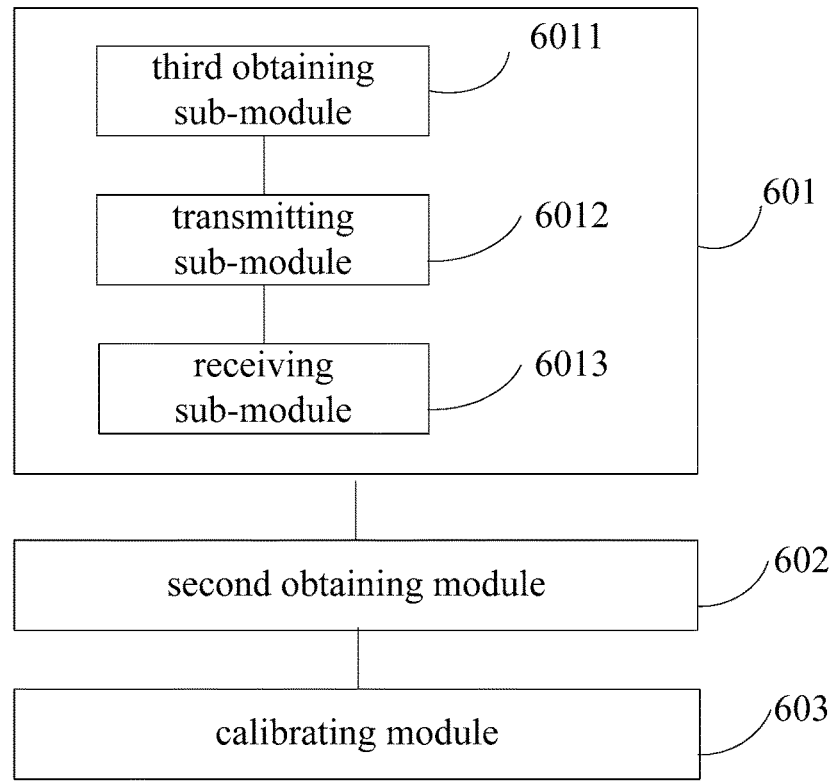
FIG. 12 is a block diagram illustrating an apparatus for calibrating a particulate matter measurement value according to one or more aspects of the present disclosure.

As shown in FIG. 12, in one or more embodiments, the first obtaining module 601 illustrated in FIG. 6 may include a third obtaining sub-module 6011, a transmitting sub-module 6012 and a receiving sub-module 6013.

The third obtaining sub-module 6011 is configured to obtain current position information.

The transmitting sub-module 6012 is configured to transmit the current position information to a target device, in which the target device is configured to obtain the current temperature-humidity parameter according to the current position information.

The receiving sub-module 6013 is configured to receive the current temperature-humidity parameter sent from the target device.

Figure 13:
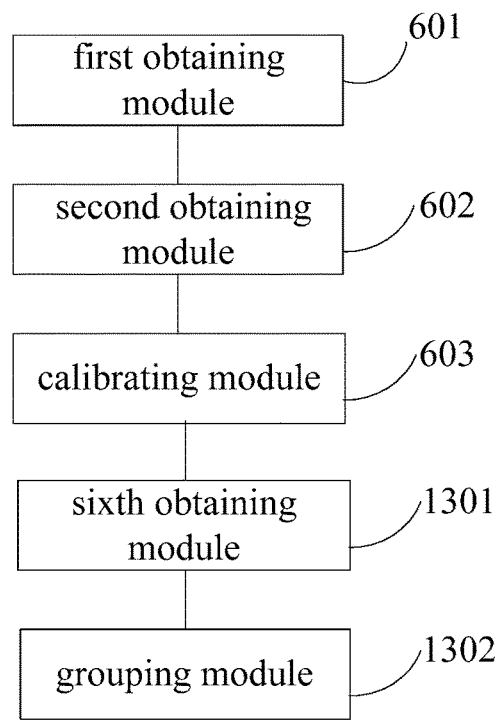
FIG. 13 is a block diagram illustrating an apparatus for calibrating a particulate matter measurement value according to one or more aspects of the present disclosure.

As shown in FIG. 13, in one or more embodiments, the apparatus illustrated in FIG. 6 may further include a sixth obtaining module 1301 and a grouping module 1302.

The sixth obtaining module 1301 is configured to obtain a plurality of preset temperature parameters and a plurality of humidity parameters before the particulate matter measurement deviation value under the current temperature-humidity parameter is obtained from the pre-stored particulate matter measurement deviation values under various temperature-humidity parameters.

The grouping module 1302 is configured to group the plurality of preset temperature parameters and the plurality of preset humidity parameters so as to obtain various temperature-humidity parameters.

According to a third aspect of the present disclosure, a device for calibrating a particulate matter measurement value is provided. The device includes a processor and a memory configured to instructions executable by the processor, in which, the processor is configured to: when a current particulate matter measurement value is obtained, obtain a current temperature-humidity parameter; obtain a particulate matter measurement deviation value under the current temperature-humidity parameter from pre-stored particulate matter measurement deviation values under various temperature-humidity parameters according to the current temperature-humidity parameter; calibrate the current particulate matter measurement value according to the particulate matter measurement deviation value under the current temperature-humidity parameter.

The above processor may also be configured as follows.

The particulate matter measurement deviation values under various temperature-humidity parameters include particulate matter measurement deviation values corresponding to various particulate matter measurement deviation value ranges under various temperature-humidity parameters.

Calibrating the current particulate matter measurement value according to the particulate matter measurement deviation value under the current temperature-humidity parameter includes: determining a target particulate matter measurement value range to which the current particulate matter measurement value belongs; obtaining a preset particulate matter measurement deviation value corresponding to the target particulate matter measurement value range from the particulate matter measurement deviation values corresponding to respective particulate matter measurement value ranges under various temperature-humidity parameters; and calibrating the current particulate matter measurement value according to the preset particulate matter measurement deviation value.

The above processor may also be configured as follows.

The method further includes: obtaining a standard particulate matter variation curve under a standard temperature-humidity parameter, wherein the standard particulate matter variation curve represents a relationship between the particulate matter measurement values and time under the standard temperature-humidity parameter; obtaining a target particulate matter variation curve under each temperature-humidity parameter, wherein the target particulate matter variation curve represents a relationship of the particulate matter measurement values and time under the temperature-humidity parameter; and obtaining the particulate matter measurement deviation value under each temperature-humidity parameter according to the standard particulate matter variation curve and the target particulate matter variation curve under each temperature-humidity parameter.

The above processor may also be configured as follows.

Obtaining the particulate matter measurement deviation value under each temperature-humidity parameter according to the standard particulate matter variation curve and the target particulate matter variation curve under each temperature-humidity parameter includes: obtaining a percentage difference variation curve of a particulate matter measurement value under each temperature-humidity parameter according to the standard particulate matter variation curve and the target particulate matter variation curve, wherein the percentage difference variation curve represents a relationship of a percentage difference between the standard particulate matter variation curve and the target particulate matter variation curve to time; and determining the particulate matter measurement deviation value under each temperature-humidity parameter according to the percentage difference variation curve under each temperature-humidity parameter.

The above processor may also be configured as follows.

Determining the particulate matter measurement deviation value under each temperature-humidity parameter according to the percentage difference variation curve under each temperature-humidity parameter includes: determining at least two particulate matter measurement value ranges; determining percentage differences of particulate matter measurement values corresponding to each particulate matter measurement value range under each temperature-humidity parameter according to the percentage difference variation curve under each temperature-humidity parameter; determining an average value of the percentage differences corresponding to each particulate matter measurement value range under each temperature-humidity parameter according to the percentage differences of particulate matter measurement values corresponding to each particulate matter measurement value range under each temperature-humidity parameter; and determining the average value of the percentage differences corresponding to each particulate matter measurement value range under each temperature-humidity parameter as the particulate matter measurement deviation value corresponding to each particulate matter measurement value range under each temperature-humidity parameter.

The above processor may also be configured as follows.

The method further includes storing the various temperature-humidity parameters, the various particulate matter measurement value ranges and the average values of percentage differences corresponding to various particulate matter measurement value ranges in a correspondence relationship.

The above processor may also be configured as follows.

Obtaining the current temperature-humidity parameters includes: obtaining current position information; transmitting the current position information to a target device, in which the target device is configured to obtain the current temperature-humidity parameter according to the current position information; receiving the current temperature-humidity parameter sent from the target device.

The above processor may also be configured as follows.

Before obtaining the particulate matter measurement deviation value under the current temperature-humidity parameter from pre-stored particulate matter measurement deviation values under various temperature-humidity parameters, the method further includes: obtaining a plurality of preset temperature parameters and a plurality of preset humidity parameters; grouping the plurality of preset temperature parameters and the plurality of preset humidity parameters so as to obtain the various temperature-humidity parameters.

Figure 14:
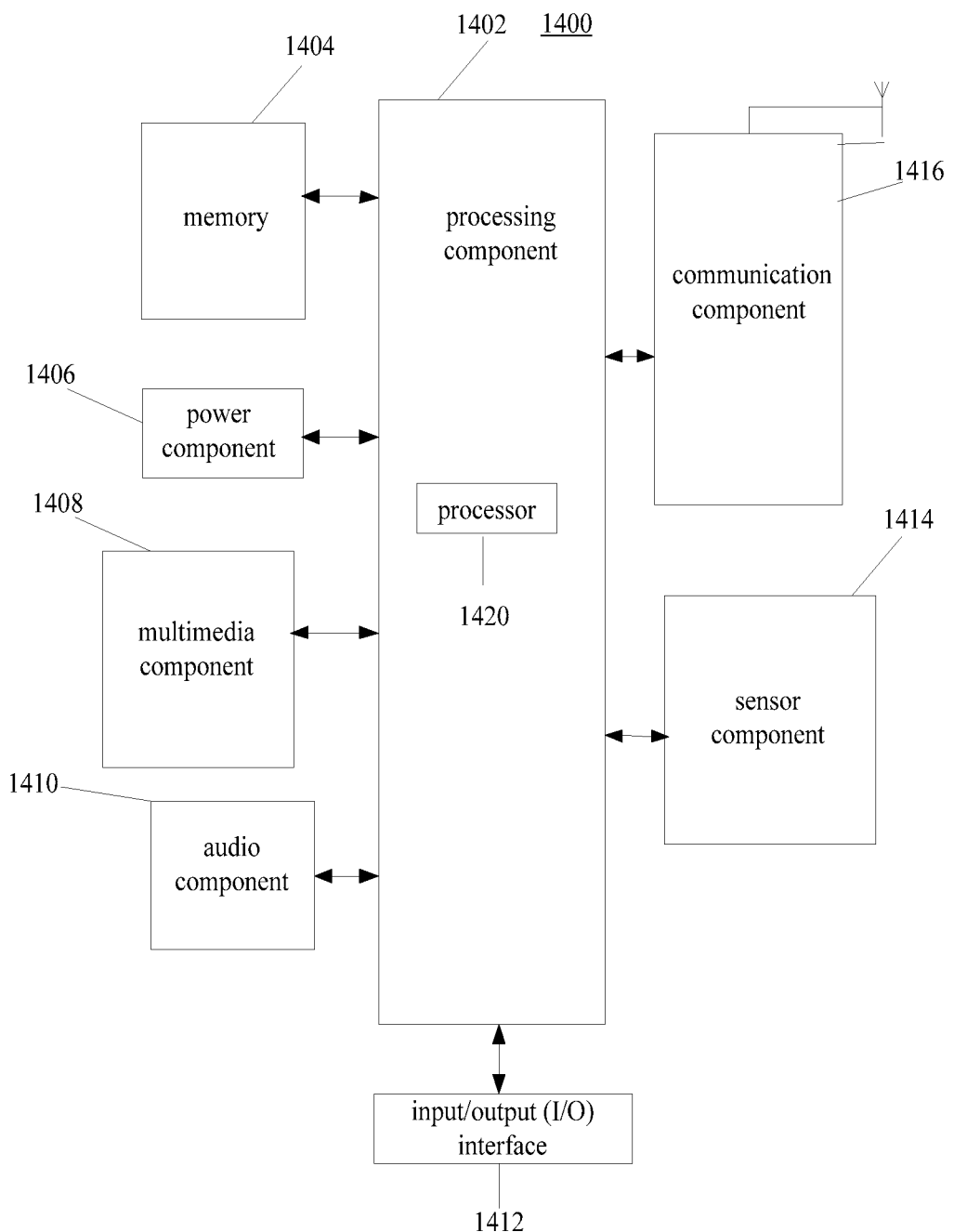
FIG. 14 is a block diagram illustrating a device for calibrating a particulate matter measurement value according to one or more aspects of the present disclosure.

FIG. 14 is a block diagram showing a device 1400 for calibrating a particulate matter measurement value according to one or more exemplary embodiments of the present disclosure. For example, device 1400 could be a mobile phone, a computer, a digital broadcast terminal, a messaging device, a gaming console, a tablet, a medical device, an exercise equipment, a personal digital assistant, and the like.

With reference to FIG. 14, the device 1400 may include one or more of the following components: a processing component 1402, a memory 1404, a power component 1406, a multimedia component 1408, an audio component 1410, an input/output (I/O) interface 1412, a sensor component 1414, and a communication component 1416.

The processing component 1402 typically controls overall operations of the device 1400, such as the operations associated with display, telephone calls, data communications, camera operations, and recording operations. The processing component 1402 may include one or more processors 1420 to execute instructions to perform all or part of the steps in the above-described methods. Moreover, the processing component 1402 may include one or more modules which facilitate the interaction between the processing component 1402 and other components. For instance, the processing component 1402 may include a multimedia module to facilitate the interaction between the multimedia component 1408 and the processing component 1402.

The memory 1404 is configured to store various types of data to support the operation of the device 1400. Examples of such data include instructions for any applications or methods operated on the device 1400, contact data, phonebook data, messages, pictures, videos, etc. The memory 1404 may be implemented using any type of volatile or non-volatile memory devices, or a combination thereof, such as a static random access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic or optical disk.

The power component 1406 provides power to various components of the device 1400. The power component 1406 may include a power management system, one or more power sources, and any other components associated with the generation, management, and distribution of power in the device 1400.

The multimedia component 1408 includes a screen providing an output interface between the device 1400 and the user. In some embodiments, the screen may include a liquid crystal display (LCD) and a touch panel (TP). If the screen includes the touch panel, the screen may be implemented as a touch screen to receive input signals from the user. The touch panel includes one or more touch sensors to sense touches, swipes, and gestures on the touch panel. The touch sensors may not only sense a boundary of a touch or swipe action, but also sense a period of time and a pressure associated with the touch or swipe action. In some embodiments, the multimedia component 1408 includes a front camera and/or a rear camera. The front camera and the rear camera may receive an external multimedia datum while the device 1400 is in an operation mode, such as a photographing mode or a video mode. Each of the front camera and the rear camera may be a fixed optical lens system or have focus and optical zoom capability.

The audio component 1410 is configured to output and/or input audio signals. For example, the audio component 1410 includes a microphone (MIC) configured to receive an external audio signal when the device 1400 is in an operation mode, such as a call mode, a recording mode, and a voice recognition mode. The received audio signal may be further stored in the memory 1404 or transmitted via the communication component 1416. In some embodiments, the audio component 1410 further includes a speaker to output audio signals.

The I/O interface 1412 provides an interface between the processing component 1402 and peripheral interface modules, such as a keyboard, a click wheel, buttons, and the like. The buttons may include, but are not limited to, a home button, a volume button, a starting button, and a locking button.

The sensor component 1414 includes one or more sensors to provide status assessments of various aspects of the device 1400. For instance, the sensor component 1414 may detect an open/closed status of the device 1400, relative positioning of components, e.g., the display and the keypad, of the device 1400, a change in position of the device 1400 or a component of the device 1400, a presence or absence of user contact with the device 1400, an orientation or an acceleration/deceleration of the device 1400, and a change in temperature of the device 1400. The sensor component 1414 may include a proximity sensor configured to detect the presence of nearby objects without any physical contact. The sensor component 1414 may also include a light sensor, such as a CMOS or CCD image sensor, for use in imaging applications. In some embodiments, the sensor component 1414 may also include an accelerometer sensor, a gyroscope sensor, a magnetic sensor, a pressure sensor, or a temperature sensor.

The communication component 1416 is configured to facilitate communication, wired or wirelessly, between the device 1400 and other devices. The device 1400 can access a wireless network based on a communication standard, such as WIFI, 2G or 3G; or a combination thereof. In one exemplary embodiment, the communication component 1416 receives a broadcast signal or broadcast associated information from an external broadcast management system via a broadcast channel. In one exemplary embodiment, the communication component 1416 further includes a near field communication (NFC) module to facilitate short-range communications. For example, the NFC module may be implemented based on a radio frequency identification (RFID) technology, an infrared data association (IrDA) technology, an ultra-wide band (UWB) technology, a Bluetooth (BT) technology, and other technologies.

In exemplary embodiments, the device 1400 may be implemented with one or more circuitries, which include application specific integrated circuits (ASICs), digital signal processors (DSPs), digital signal processing devices (DSPDs), programmable logic devices (PLDs), field programmable gate arrays (FPGAs), controllers, micro-controllers, microprocessors, or other electronic components, for performing the above-described methods. The device 1400 may use the circuitries in combination with the other hardware or software components for executing the method above. Each module, sub-module, unit, or sub-unit disclosed above may be implemented at least partially using the one or more circuitries.

In exemplary embodiments, there is also provided a non-transitory computer readable storage medium including instructions, such as the memory 1404 including instructions, the above instructions are executable by the processor 1420 in the device 1400, for performing the above-described methods. For example, the non-transitory computer-readable storage medium may be a ROM, a RAM, a CD-ROM, a magnetic tape, a floppy disc, an optical data storage device, and the like.

A non-transitory computer readable storage medium, having instructions stored therein that, when executed by a processor of the above device 1400, cause the device 1400 to perform a method for calibrating a particulate matter measurement value, the method including: when a current particulate matter measurement value is obtained, obtaining a current temperature-humidity parameter; obtaining a particulate matter measurement deviation value under the current temperature-humidity parameter from pre-stored particulate matter measurement deviation values under various temperature-humidity parameters according to the current temperature-humidity parameter; calibrating the current particulate matter measurement value according to the particulate matter measurement deviation value under the current temperature-humidity parameter.

In one or more embodiments, the particulate matter measurement deviation values under different temperature-humidity parameters may further include particulate matter measurement deviation values corresponding to various particulate matter measurement deviation value ranges under various temperature-humidity parameters, and calibrating the current particulate matter measurement value according to the particulate matter measurement deviation value under the current temperature-humidity parameter may include: determining a target particulate matter measurement value range to which the current particulate matter measurement value belongs; obtaining a preset particulate matter measurement deviation value corresponding to the target particulate matter measurement value range from the particulate matter measurement deviation values corresponding to different particulate matter measurement value ranges under different temperature-humidity parameters; and calibrating the current particulate matter measurement value according to the preset particulate matter measurement deviation value.

In one or more embodiments, the method further includes: obtaining a standard particulate matter variation curve under a standard temperature-humidity parameter, in which the standard particulate matter variation curve represents a relationship between the particulate matter measurement values and the time under the standard temperature-humidity parameter; obtaining a target particulate matter variation curve under each temperature-humidity parameter, in which the target particulate matter variation curve represents a relationship between the particulate matter measurement values and the time under the temperature-humidity parameter; obtaining the particulate matter measurement deviation value under each temperature-humidity parameter according to the standard particulate matter variation curve and the target particulate matter variation curve under each temperature-humidity parameter.

In one or more embodiments, obtaining the particulate matter measurement deviation value under each temperature-humidity parameter according to the standard particulate matter variation curve and the target particulate matter variation curve under each temperature-humidity parameter includes: obtaining a percentage difference variation curve of a particulate matter measurement value under each temperature-humidity parameter according to the standard particulate matter variation curve and the target particulate matter variation curve, wherein the percentage difference variation curve represents a relationship of a percentage difference between the standard particulate matter variation curve and the target particulate matter variation curve to time; and determining the particulate matter measurement deviation value under each temperature-humidity parameter according to the percentage difference variation curve under each temperature-humidity parameter.

In one or more embodiments, determining the particulate matter measurement deviation value under each temperature-humidity parameter according to the percentage difference variation curve under each temperature-humidity parameter includes: determining at least two particulate matter measurement value ranges; determining percentage differences of particulate matter measurement values corresponding to each particulate matter measurement value range under each temperature-humidity parameter according to the percentage difference variation curve under each temperature-humidity parameter; determining an average value of the percentage differences corresponding to each particulate matter measurement value range under each temperature-humidity parameter according to the percentage differences of particulate matter measurement values corresponding to each particulate matter measurement value range under each temperature-humidity parameter; and determining the average value of the percentage differences corresponding to each particulate matter measurement value range under each temperature-humidity parameter as the particulate matter measurement deviation value corresponding to each particulate matter measurement value range under each temperature-humidity parameter.

In one or more embodiments, the method further includes storing the various temperature-humidity parameters, the various particulate matter measurement value ranges and the average values of percentage differences corresponding to various particulate matter measurement value ranges in a correspondence relationship.

In one or more embodiments, obtaining the current temperature-humidity parameter includes: obtaining current position information; transmitting the current position information to a target device, in which the target device is configured to obtain the current temperature-humidity parameter according to the current position information; receiving the current temperature-humidity parameter sent from the target device.

In one or more embodiments, before obtaining the particulate matter measurement deviation value under the current temperature-humidity parameter from pre-stored particulate matter measurement deviation values under various temperature-humidity parameters, the method further includes: obtaining a plurality of preset temperature parameters and a plurality of preset humidity parameters; grouping the plurality of preset temperature parameters and the plurality of preset humidity parameters to obtain various temperature-humidity parameters.

The terminology used in the present disclosure is for the purpose of describing exemplary embodiments only and is not intended to limit the present disclosure. As used in the present disclosure and the appended claims, the singular forms "a," "an" and "the" are intended to include the plural forms as well, unless the context clearly indicates otherwise. It shall also be understood that the terms "or" and "and/or"

used herein are intended to signify and include any or all possible combinations of one or more of the associated listed items, unless the context clearly indicates otherwise.

It shall be understood that, although the terms "first," "second," "third," etc. may be used herein to describe various information, the information should not be limited by these terms. These terms are only used to distinguish one category of information from another. For example, without departing from the scope of the present disclosure, first information may be termed as second information; and similarly, second information may also be termed as first information. As used herein, the term "if" may be understood to mean "when" or "upon" or "in response to" depending on the context.

Reference throughout this specification to "one embodiment," "an embodiment," "exemplary embodiment," or the like in the singular or plural means that one or more particular features, structures, or characteristics described in connection with an embodiment is included in at least one embodiment of the present disclosure. Thus, the appearances of the phrases "in one embodiment" or "in an embodiment," "in an exemplary embodiment," or the like in the singular or plural in various places throughout this specification are not necessarily all referring to the same embodiment. Furthermore, the particular features, structures, or characteristics in one or more embodiments may be combined in any suitable manner.

Other embodiments of the invention will be apparent to those skilled in the art from consideration of the specification and practice of the invention disclosed here. This application is intended to cover any variations, uses, or adaptations of the invention following the general principles thereof and including such departures from the present disclosure as come within known or customary practice in the art. It is intended that the specification and examples be considered as exemplary only, with a true scope and spirit of the invention being indicated by the following claims.

It will be appreciated that the present invention is not limited to the exact construction that has been described above and illustrated in the accompanying drawings and that various modifications and changes can be made without departing from the scope thereof. It is intended that the scope of the invention only be limited by the appended claims.

What is claimed is:

1. A method for calibrating a particulate matter measurement value, comprising:
    obtaining a current particulate matter measurement value and obtaining a current temperature-humidity parameter associated with the current particulate matter measurement value;
    obtaining a particulate matter measurement deviation value corresponding to the current temperature-humidity parameter from pre-stored particulate matter measurement deviation values corresponding to various temperature-humidity parameters using the current temperature-humidity parameter, wherein the particulate matter measurement deviation value is obtained using a standard particulate matter variation curve corresponding to a standard temperature-humidity parameter, and the standard particulate matter variation curve is obtained by blowing dusts into an experiment box; and
    calibrating the current particulate matter measurement value according to the particulate matter measurement deviation value corresponding to the current temperature-humidity parameter; and
    wherein obtaining the current temperature-humidity parameter comprises:
    obtaining current position information;
    transmitting the current position information to a target device, wherein the target device is configured to obtain the current temperature-humidity parameter according to the current position information; and
    receiving the current temperature-humidity parameter sent from the target device.

2. The method according to claim 1, wherein the particulate matter measurement deviation values comprise:
    particulate matter measurement deviation values corresponding to respective particulate matter measurement value ranges under various temperature-humidity parameters.

3. The method according to claim 2, wherein calibrating the current particulate matter measurement value according to the particulate matter measurement deviation value corresponding to the current temperature-humidity parameter comprises:
    determining a target particulate matter measurement value range to which the current particulate matter measurement value belongs;
    obtaining a preset particulate matter measurement deviation value corresponding to the target particulate matter measurement value range from the particulate matter measurement deviation values corresponding to respective particulate matter measurement value ranges under various temperature-humidity parameters; and
    calibrating the current particulate matter measurement value according to the preset particulate matter measurement deviation value.

4. The method according to claim 1, further comprising:
    obtaining the standard particulate matter variation curve corresponding to the standard temperature-humidity parameter, wherein the standard particulate matter variation curve represents a first relationship between the particulate matter measurement values and time corresponding to the standard temperature-humidity parameter;
    obtaining a target particulate matter variation curve corresponding to a temperature-humidity parameter, wherein the target particulate matter variation curve represents a second relationship of the particulate matter measurement values and time corresponding to the temperature-humidity parameter; and
    obtaining the particulate matter measurement deviation value corresponding to the temperature-humidity parameter according to the standard particulate matter variation curve and the target particulate matter variation curve corresponding to the temperature-humidity parameter.

5. The method according to claim 4, wherein obtaining the particulate matter measurement deviation value corresponding to the temperature-humidity parameter according to the standard particulate matter variation curve and the target particulate matter variation curve corresponding to the temperature-humidity parameter comprises:
    obtaining a percentage difference variation curve of a particulate matter measurement value corresponding to the temperature-humidity parameter according to the standard particulate matter variation curve and the target particulate matter variation curve, wherein the percentage difference variation curve represents a relationship of a percentage difference between the standard particulate matter variation curve and the target particulate matter variation curve to time; and determining the particulate matter measurement deviation value corresponding to the temperature-humidity parameter according to the percentage difference variation curve corresponding to the temperature-humidity parameter.

6. The method according to claim 5, wherein determining the particulate matter measurement deviation value corresponding to the temperature-humidity parameter according to the percentage difference variation curve corresponding to the temperature-humidity parameter comprises:
   determining at least two particulate matter measurement value ranges;
   determining percentage differences of particulate matter measurement values corresponding to each particulate matter measurement value range under each temperature-humidity parameter according to the percentage difference variation curve under each temperature-humidity parameter;
   determining an average value of the percentage differences corresponding to each particulate matter measurement value range under each temperature-humidity parameter according to the percentage differences of particulate matter measurement values corresponding to each particulate matter measurement value range under each temperature-humidity parameter; and
   determining the average value of the percentage differences corresponding to each particulate matter measurement value range under each temperature-humidity parameter as the particulate matter measurement deviation value corresponding to each particulate matter measurement value range under each temperature-humidity parameter.

7. The method according to claim 6, further comprising:
   storing the various temperature-humidity parameters, the various particulate matter measurement value ranges and the average values of percentage differences corresponding to various particulate matter measurement value ranges in a correspondence relationship.

8. The method according to claim 1, wherein before obtaining the particulate matter measurement deviation value corresponding to the current temperature-humidity parameter from pre-stored particulate matter measurement deviation values under various temperature-humidity parameters, the method further comprises:
   obtaining a plurality of preset temperature parameters and a plurality of preset humidity parameters;
   grouping the plurality of preset temperature parameters and the plurality of preset humidity parameters to obtain various temperature-humidity parameters.

9. A device for calibrating a particulate matter measurement value, comprising:
   a processor; and
   a memory configured to store instructions executable by the processor,
   wherein, the processor is configured to:
   when a current particulate matter measurement value is obtained, obtain a current temperature-humidity parameter;
   obtain a particulate matter measurement deviation value corresponding to the current temperature-humidity parameter from pre-stored particulate matter measurement deviation values corresponding to various temperature-humidity parameters according to the current temperature-humidity parameter, wherein the particulate matter measurement deviation value is obtained using a standard particulate matter variation curve corresponding to a standard temperature-humidity parameter, and the standard particulate matter variation curve is obtained by blowing dusts into an experiment box;
   calibrate the current particulate matter measurement value according to the particulate matter measurement deviation value corresponding to the current temperature-humidity parameter;
   obtain current position information;
   transmit the current position information to a target device, wherein the target device is configured to obtain the current temperature-humidity parameter according to the current position information; and
   receive the current temperature-humidity parameter sent from the target device.

10. The device according to claim 9, wherein the particulate matter measurement deviation values comprise:
    particulate matter measurement deviation values corresponding to respective particulate matter measurement value ranges under various temperature-humidity parameters.

11. The device according to claim 10, wherein the processor is configured to:
    determine a target particulate matter measurement value range to which the current particulate matter measurement value belongs;
    obtain a preset particulate matter measurement deviation value corresponding to the target particulate matter measurement value range from the particulate matter measurement deviation values corresponding to respective particulate matter measurement value ranges under various temperature-humidity parameters;
    calibrate the current particulate matter measurement value according to the preset particulate matter measurement deviation value.

12. The device according to claim 9, wherein the processor is further configured to:
    obtain the standard particulate matter variation curve under the standard temperature-humidity parameter, wherein the standard particulate matter variation curve represents a relationship between the particulate matter measurement values and time corresponding to the standard temperature-humidity parameter;
    obtain a target particulate matter variation curve under a temperature-humidity parameter, wherein the target particulate matter variation curve represents a relationship of the particulate matter measurement values and time corresponding to the temperature-humidity parameter;
    obtain the particulate matter measurement deviation value corresponding to the temperature-humidity parameter according to the standard particulate matter variation curve and the target particulate matter variation curve corresponding to the temperature-humidity parameter.

13. The device according to claim 12, wherein the processor is configured to:
    obtain a percentage difference variation curve of a particulate matter measurement value corresponding to the temperature-humidity parameter according to the standard particulate matter variation curve and the target particulate matter variation curve, wherein the percentage difference variation curve represents a relationship of a percentage difference between the standard particulate matter variation curve and the target particulate matter variation curve to time; and
    determine the particulate matter measurement deviation value corresponding to the temperature-humidity parameter according to the percentage difference variation curve corresponding to the temperature-humidity parameter.

14. The device according to claim 13, wherein the processor is configured to:
   determine at least two particulate matter measurement value ranges;
   determine percentage differences of particulate matter measurement values corresponding to each particulate matter measurement value range under each temperature-humidity parameter according to the percentage difference variation curve under each temperature-humidity parameter;
   determine an average value of the percentage differences corresponding to each particulate matter measurement value range under each temperature-humidity parameter according to the percentage differences of particulate matter measurement values corresponding to each particulate matter measurement value range under each temperature-humidity parameter; and
   determine the average value of the percentage differences corresponding to each particulate matter measurement value range under each temperature-humidity parameter as the particulate matter measurement deviation value corresponding to each particulate matter measurement value range under each temperature-humidity parameter.

15. The device according to claim 14, wherein the processor is further configured to:
   store the various temperature-humidity parameters, the various particulate matter measurement value ranges and the average values of percentage differences corresponding to various particulate matter measurement value ranges in a correspondence relationship.

16. The device according to claim 9, wherein the processor is further configured to:
   obtain a plurality of preset temperature parameters and a plurality of preset humidity parameters;
   group the plurality of preset temperature parameters and the plurality of preset humidity parameters to obtain various temperature-humidity parameters.

17. A non-transitory computer readable storage medium, having stored therein instructions that, when executed by a processor of a device, cause the device to perform a method for calibrating a particulate matter measurement value, the method comprising:
   when a current particulate matter measurement value is obtained, obtaining a current temperature-humidity parameter;
   obtaining a particulate matter measurement deviation value corresponding to the current temperature-humidity parameter from pre-stored particulate matter measurement deviation values corresponding to various temperature-humidity parameters according to the current temperature-humidity parameter, wherein the particulate matter measurement deviation value is obtained using a standard particulate matter variation curve corresponding to a standard temperature-humidity parameter, and the standard particulate matter variation curve is obtained by blowing dusts into an experiment box; and
   calibrating the current particulate matter measurement value according to the particulate matter measurement deviation value corresponding to the current temperature-humidity parameter; and
   wherein obtaining the current temperature-humidity parameter comprises:
   obtaining current position information;
   transmitting the current position information to a target device, wherein the target device is configured to obtain the current temperature-humidity parameter according to the current position information; and
   receiving the current temperature-humidity parameter sent from the target device.

18. The non-transitory computer readable storage medium according to claim 17,
   wherein the particulate matter measurement deviation values comprise: particulate matter measurement deviation values corresponding to respective particulate matter measurement value ranges under various temperature-humidity parameters; and
   wherein calibrating the current particulate matter measurement value according to the particulate matter measurement deviation value corresponding to the current temperature-humidity parameter comprises:
   determining a target particulate matter measurement value range to which the current particulate matter measurement value belongs;
   obtaining a preset particulate matter measurement deviation value corresponding to the target particulate matter measurement value range from the particulate matter measurement deviation values corresponding to respective particulate matter measurement value ranges under various temperature-humidity parameters; and
   calibrating the current particulate matter measurement value according to the preset particulate matter measurement deviation value.

* * * * *